United States Patent [19]

Brunnée et al.

[11] 4,178,507

[45] Dec. 11, 1979

[54] IONIZATION OF ORGANIC SUBSTANCES ON CONVEYOR MEANS IN MASS SPECTROMETER

[75] Inventors: Curt Brunnée, Platjenwerbe; Jochen Franzen, Wildeshausen; Stefan Meier, Bremen, all of Fed. Rep. of Germany

[73] Assignee: Varian Mat GmbH, Bremen, Fed. Rep. of Germany

[21] Appl. No.: 855,579

[22] Filed: Nov. 29, 1977

[30] Foreign Application Priority Data

Nov. 29, 1976 [DE] Fed. Rep. of Germany ....... 2654057

[51] Int. Cl.$^2$ ........................ B01D 59/54; H01J 39/34
[52] U.S. Cl. ................................ 250/282; 250/288; 73/61.1 C; 250/423 R
[58] Field of Search .......... 250/281, 282, 288, 423 R, 250/425, 442, 453, 454; 210/31; 73/61.1 C

[56] References Cited

U.S. PATENT DOCUMENTS

| | | | |
|---|---|---|---|
| 3,308,292 | 3/1967 | Ardenne | 250/423 |
| 4,055,987 | 11/1977 | McFadden | 73/61.1 C |
| 4,075,475 | 2/1978 | Risby et al. | 250/282 |

OTHER PUBLICATIONS

Benninghoven et al. 'Secondary-Ion Emission of Amino Acids', Applied Phy., vol. 11, Sept. 26, pp. 35-39.

*Primary Examiner*—Bruce C. Anderson
*Attorney, Agent, or Firm*—Sughrue, Rothwell, Mion, Zinn and Macpeak

[57] ABSTRACT

Organic samples 10 coming from a liquid chromatograph 11 are deposited on a conveyor belt 13 which transports them into a vacuum chamber at the entry end of a mass spectrometer. The samples are ionized directly on the belt by ion bombardment or using a gaseous charge carrier. Ionization is enhanced by applying an oxide layer to the belt, by neutralizing the image force, and by vaporizing alkali atoms on the belt to reduce the ionization potential.

14 Claims, 2 Drawing Figures

IONIZATION OF ORGANIC SUBSTANCES ON CONVEYOR MEANS IN MASS SPECTROMETER

BACKGROUND OF THE INVENTION

The invention relates to a process for the ionization of samples of organic substances transported by a conveyor belt from a liquid chromatograph (LC) into the vacuum area of a mass spectrometer (MS).

The coupling or combination of mass spectrometers with other analyzing devices has been known. The combination of a mass spectrometer with a liquid chromatograph is particularly advantageous since as a result, the good separating effect of the liquid chromatograph coincides with the good specificity of substance of the mass spectrometer.

While in a known coupling of a gas chromatograph with a mass spectrometer a separation of the substances is carried out in the gaseous state, and therefore the good volatility of such substances is a prerequisite, the LC/MS coupling will also permit the analysis of difficult to vaporize substances. The prerequisite, however, is that these substances may be dissolved and ionized in the mass spectrometer. In particular, many bio-chemically and medically important compounds belong to groups of these difficult to vaporize substances.

The consecutive connection of an LC and MS has already been proposed. In the construction of such a combination one may, for example, proceed in such a way that the organic substance contained in a solvent is applied along with the solvent to a conveyor belt or wire which feeds the sample to a connected mass spectrometer. The conveyor belt leads up into the vacuum area of the mass spectrometer. This vacuum area is limited against the infeed area of the sample by underpressure sluices and suitable gaskets or packings. Prior to the entry of the sample into the vacuum area of the mass spectrometer the solvent is evaporated so that the dried sample on the belt is conveyed into the mass spectrometer.

The ionization of the organic sample reaching the mass spectrometer in this way constitutes a special problem. In this connection only electron impact ionization is known, which assumes that the sample evaporates in the vacuum area and is then ionized by electronic impact. The conveyor belt is properly heated for the evaporation of the sample.

Electronic impact ionization is particularly unfavorable or unsuitable in the investigation of sensitive organic substances. The molecule that is to be ionized absorbs internal energy twice in the case of this ionization process. Even during evaporation by heating, enough inner energy is absorbed so that a complete decomposition may occur in particularly sensitive substances. The additionally fed-in energy (beyond the ionization energy) during the electronic impact-ionization causes a further strong fragmentation of the molecules so that the mass spectra produced are no longer characteristic of the starting substance. For this reason, the LC/MS coupling combined with a conveyor belt has not yet gained acceptance in practice corresponding to the potential importance of such combination.

SUMMARY OF THE INVENTION

The invention is based on a process for the ionization of sensitive organic samples which are fed to an MS on a conveyor belt or a transportation wire coming from an LC in such a way that the mass spectrometric destruction or impairment of the molecules to be ionized is avoided. The process of the invention is characterized in that the sample is ionized directly on the conveyor belt or transportation wire, and the ions are removed from it.

Different ionization processes are suitable for the ionization of the substance on the conveyor belt or transportation wire. Ionization by ion bombardment of the sample directly on the conveyor belt is particularly appropriate. This ionization process is disclosed in the publication "Secondary - Ion Emission of Amino Acids" by P. Penninghoven et al. in the journal "*APPLIED PHYSICS,*" 11/1976, pages 35–39 concerning experiments for the ionization of substances, such as amino acid, etc., in water, by submerging a foil into the solution and subsequent treatment by ion-bombardment. The invention thus realizes that samples on a conveyor belt or transportation wire coming from an LC are ionizable directly on said transportation means by ion bombardment.

The invention is based furthermore on the realization that in case of an ionization of the substance directly on the conveyor belt only a fraction of the complete ionization energy needs to be used, namely the difference between the full ionization energy and the work function of the electrons from the conveyor belt or transportation wire. As a result of this, the ionization is greatly facilitated. In order to support this effect, measures have been taken according to the invention to increase the electron work function or lower the ionization potential. These measures include the neutralization of a so-called image force by a relatively small electric field of, for example, about $10^4$ V/cm applied to the surface of the conveyor belt or transportation wire. Larger electric fields will support the separation of the absorbed ions from the conveyor belt. A thin wire mesh or a pin hole diaphragm with a voltage in the order of 1-2 kV may be attached for this purpose at a small distance from the conveyor belt or the transportation wire (1 to 2 mm).

As an alternative, ionization may also be carried out by charge carriers introduced into an ionization space, especially gaseous charge carriers such as, for example, methane ($CH_5^+$). These charge carriers, at an increased pressure of 1 torr and an elevated temperature of 200° C. within the ionization space, for example, will also bring about an ionization of the sample directly on the conveyor belt or transportation wire. At the same time, the conveyor belt with the sample passes through the ionization space.

The conveyor means according to the invention are formed from a material with a high electronic work function, such as platinum, nickel rhenium, etc.

A particular characteristic of the invention lies in the fact that the electron work function is increased by special measures. These include treating the surface of the conveyor belt or the transportation wire prior to or after entry into the vacuum area of the mass spectrometer in the sense of a "contamination" of the surface. This conditioning may take place, for example, by the application of an oxidation layer. Such surface treatment of the conveyor agent degrades relatively quickly in the high vacuum, but by continuously revolving the conveyor belt or transportation wire one can ensure that a "freshly" treated surface of the conveying means will reach the vacuum area.

An additional treatment may also be accomplished to decrease the ionization potential by the addition of certain substances to the organic substances on the conveyor belt or the transportation wire. For this purpose, for example, alkali atoms may be vaporized onto the conveyor belt or transportation wire, or alternatively substances such as potassium, sodium, cesium, lithium etc. may be used.

DETAILED DESCRIPTION OF THE PREFERRED EMBODIMENTS

Figure 1:
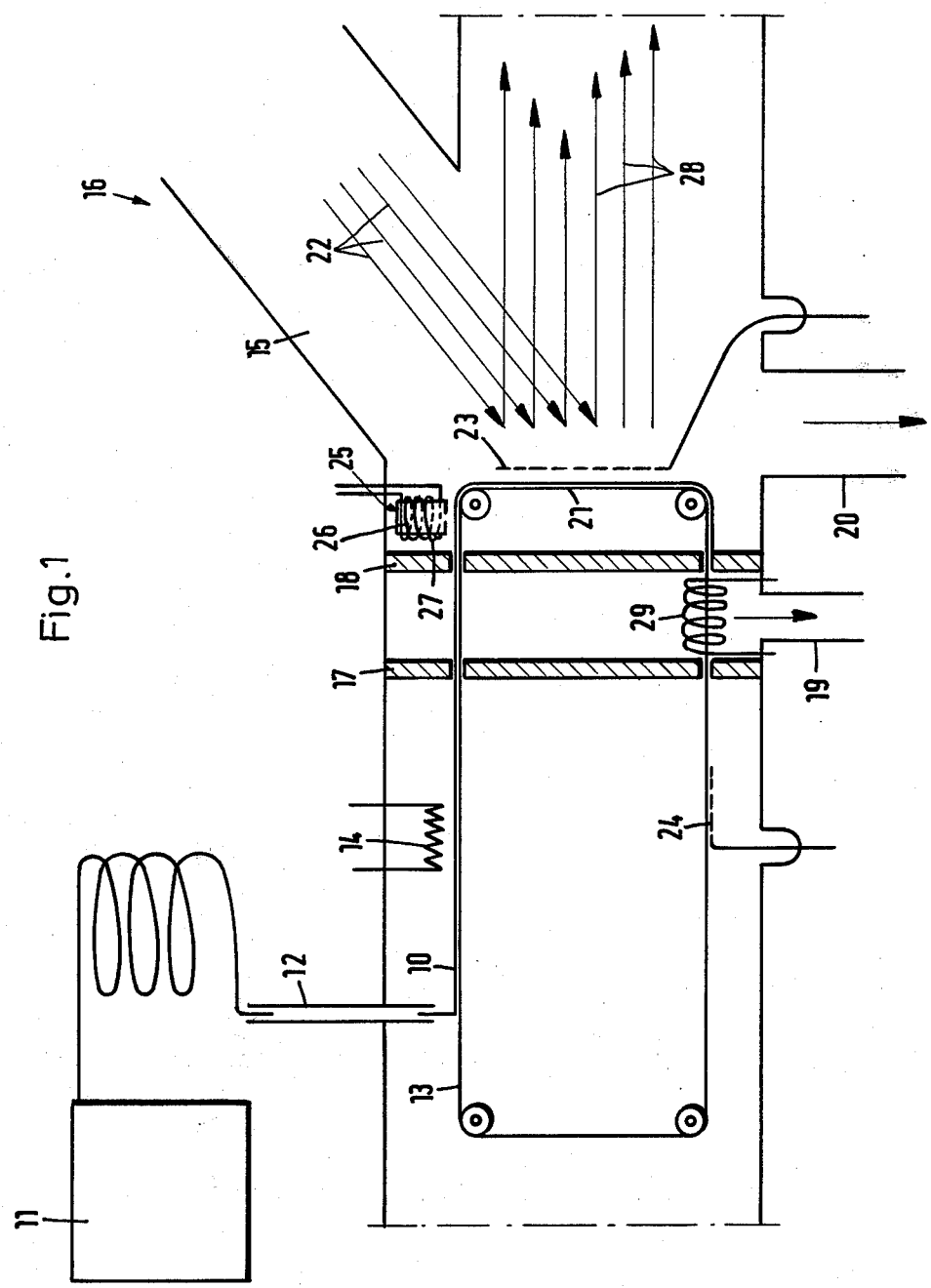
FIG. 1 shows a schematic embodiment of the invention featuring ionization by ion bombardment.

Referring now to the drawings, an organic sample 10, contained in a solvent, is applied by a liquid chromatograph 11 through a pipe 12 for the samples to an endless conveyor belt 13 or a transportation wire. The latter is preferably driven continuously in a clockwise direction.

The solvent is evaporated from the conveyor belt 13 by a heater 14. The dried sample 10 is then carried by the conveyor belt 13 into a vacuum area 15 (FIG. 1) of a mass spectromater 16. The entry of the conveyor belt 13 into this vacuum area 15 as well as its exit from this area is protected against any loss of vacuum by two gaskets or packings 17 and 18. The area between the gaskets 17, 18 may be evacuated by a connection 19 to a first vacuum pump (not shown). A second vacuum pump is coupled by a connection 20 to the mass spectrometer 16.

The sample 10 is ionized directly on the conveyor belt 13 in the vacuum area 15 of the mass spectrometer 16. The ions are then removed from the conveyor belt 13 and are fed in the customary manner to an analyzer. This connected part of the mass spectrometer 16, not shown, may have any conventional form.

The ionization of the sample 10 on the conveyor belt 13 may take place in different ways. In the embodiment of FIG. 1, ionization by ion bombardment is shown schematically, whereby ion beams 22 with kinetic energies of a few keV are directed at the sample 10. As an alternative, ion bombardment may also take place with heavy ions of high energy (for example, many MeV). In that case some secondary ions 28 may escape to the analyzer.

In order to facilitate the separation of the ions from the surface of the conveyor belt 13 or transportation wire, the image force between the ions and a mirror (image) charge is neutralized by an external electric field. As a result, the energy required for opening the dipole is prevented from being fed in as random collison energy, which increases the danger of decomposition of the molecules.

In the area of the vertical or erect part 21 of the conveyor belt 13 a thin screen 23 is disposed at as light distance from the surface of the conveyor belt. This screen 23, consisting for example of gold or platinum, is supplied with a voltage to produce an electric field of, for example, about $10^4$ V/cm. The distance of the screen 23 from the belt surface is about 1 to 2 mm.

The conveyor belt 13 is subjected to a special treatment by which the work function is increased. Thus, a thin oxide layer is applied as a surface contaminant to the conveyor belt. In the present embodiment, a cathode 24 is disposed adjacent the conveyor belt outside of the vacuum area 15 and prior to the sample application. This cathode 24 causes the application of an oxide layer by glow discharge (anodic oxidation). Since the conveyor belt 13, after leaving the vacuum area 15, is always newly treated in this manner, the effect achieved of increasing the work function is continuously maintained. The oxide layer may be formed of the material of the conveyor belt 13, but may also be formed of a foreign material.

A further improvement of the ionization effect is brought about by lowering the ionization potential in a treatment zone of the conveyor belt 13 between the gaskets and after application of the sample 10. For this purpose, evaporation means 25 have been provided, which may comprise an oven 26 and a heater 27 which serves to vaporize alkali atoms. As a result, addition complexes from alkali atoms with organic energy will develop. For example, potassium, sodium, cesium, lithium, etc., are suitable for this purpose.

A heater 29 is also installed between the gaskets 17 and 18, by which an residue on the conveyor belt 13 or transportation wire is removed after the ionization process.

Figure 2:
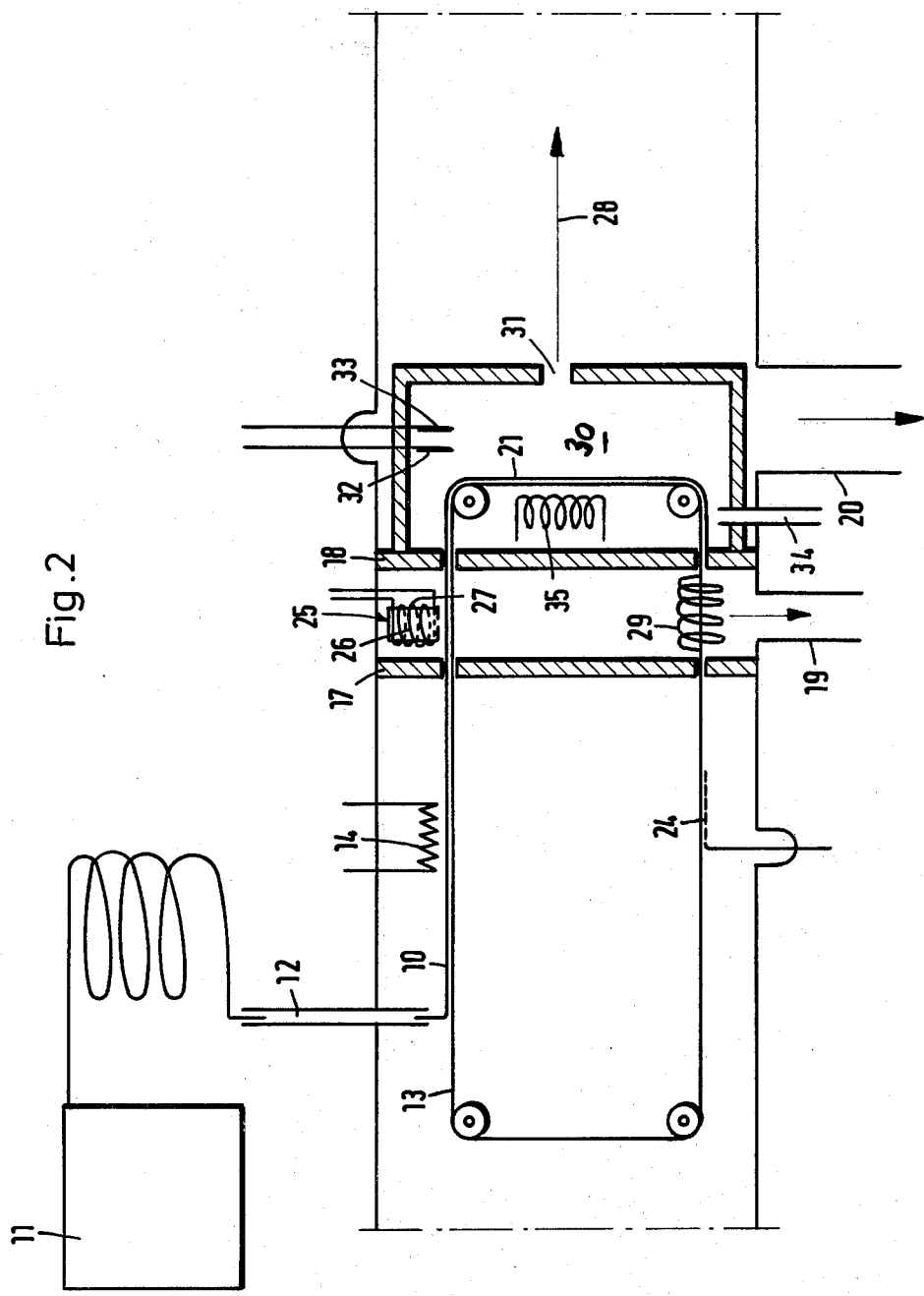
FIG. 2 shows a diagram similar to FIG. 1, but featuring ionization by gaseous charge carriers.

In the embodiment of FIG. 2, a special, smaller ionization space 30 is formed by homologous walls. The conveyor belt 13 with the applied sample 10 passes through this ionization space 30, and the otherwise sealed space has an exit aperture 31 for the ions.

Two electrodes 32 and 33 project into the ionization space 30, and a voltage of about 2 kV is applied across them. An inlet tube 34 is provided for a gas which serves as a charge carrier inside of the ionization space. A heater 35 is also installed within the ionization space 30 to produce a temperature of about 200° C., which is required for ionizing the sample 10 on the conveyor belt 13.

According to this alternative embodiment, ionization takes place as a result of the direct interaction of the sample 10 with the charge carrier under a thermal influence. The gas, such as methane, is ionized by the electrodes 32, 33 to about 1 KeV. The production of the charge carrier may also be performed by electrons emitted by a cathode instead of the electric discharge between the electrodes 32, 33. An excess pressure of about 1 torr is also maintained in the ionization space 30 for enhancing the ionization effect. The ions emerge through the outlet opening 31 and are then analyzed in the manner described above.

What is claimed is:

1. A method for analyzing samples of organic substances in a mass spectrometer comprising the steps of:
    transferring a sample of a substance to be analyzed in a solvent from a liquid chromatograph onto a moving continuous belt;
    vaporizing the solvent on the belt;
    moving the belt so as to move the sample into an ionization chamber associated with a mass spectrometer;
    ionizing the sample directly on the belt in the ionization chamber; and
    removing the ions from the belt and conducting them into the mass spectrometer.

2. A process as in claim 1, wherein the detaching of the ions from the surface of the conveyor means is facilitated by the neutralization of the "image force" between the ion charge and the image charge.

3. A process as in claim 2, wherein an electric field of about $10^4$ V/cm is applied to the surface of the conveyor means.

4. A process as in claim 2, characterized in that an electrically charged screen is disposed at a slight distance from the surface of the conveyor means.

5. A process as in claim 1, wherein the sample (10) is ionized on the conveyor means by the interaction of slow charge carriers introduced into or produced within an ionization space through which said conveyor means passes.

6. A process as in claim 5, wherein a gas, such as methane, is introduced into the ionization space as a charge carrier at an increased pressure of about 1 torr and at an increased temperature of about 200° C. on the conveyor means.

7. A process as in claim 1, wherein the sample (10) is ionized directly on the conveyor means by ion bombardment.

8. A process as in claim 1, wherein the sample is ionized during continuous movement of the conveyor means.

9. A process as in claim 1, wherein the conveyor means consists of a material with a high electron work function.

10. A process as in claim 9, wherein the conveyor means is treated to increase the electron work function.

11. A process as in claim 10, wherein an oxidation layer is applied to the conveyor means to increase the electron work function.

12. A process as in claim 1, wherein substances are applied to the conveyor means to reduce the ionization potential.

13. A process as in claim 12, wherein alkali atoms are vaporized onto the conveyor means in the vacuum area after the application of the sample.

14. A process as in claim 1, wherein residues remaining on the conveyor means after the ionization process are removed from said conveyor belt by heating.

* * * * *